United States Patent
Hirai et al.

(10) Patent No.: US 12,274,420 B2
(45) Date of Patent: Apr. 15, 2025

(54) MEDICAL SYSTEM, COMMUNICATION METHOD, IMAGING DEVICE, INFORMATION PROCESSING DEVICE, AND ENDOSCOPE SYSTEM

(71) Applicant: SONY GROUP CORPORATION, Tokyo (JP)

(72) Inventors: Takayoshi Hirai, Tokyo (JP); Takuya Nakamura, Tokyo (JP); Shinji Katsuki, Tokyo (JP); Motoaki Kobayashi, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 613 days.

(21) Appl. No.: 17/615,957

(22) PCT Filed: Jun. 3, 2020

(86) PCT No.: PCT/JP2020/021968
§ 371 (c)(1),
(2) Date: Dec. 2, 2021

(87) PCT Pub. No.: WO2020/250776
PCT Pub. Date: Dec. 17, 2020

(65) Prior Publication Data
US 2022/0322921 A1  Oct. 13, 2022

(30) Foreign Application Priority Data
Jun. 11, 2019 (JP) .................................. 2019-108699

(51) Int. Cl.
*A61B 1/04* (2006.01)
*A61B 1/00* (2006.01)
(Continued)

(52) U.S. Cl.
CPC .......... *A61B 1/042* (2013.01); *A61B 1/00016* (2013.01); *H04N 23/661* (2023.01); *H04N 23/555* (2023.01)

(58) Field of Classification Search
CPC . A61B 1/00154; A61B 1/042; A61B 1/00016; A61B 17/34; H04N 23/661; H04N 23/555; H04B 13/00
See application file for complete search history.

(56) References Cited

U.S. PATENT DOCUMENTS

| 5,328,458 A | 7/1994 | Sekino et al. |
| 7,048,686 B2 * | 5/2006 | Kameya ................... A61B 1/05 600/179 |

(Continued)

FOREIGN PATENT DOCUMENTS

| CN | 101322640 A | 12/2008 |
| CN | 101662992 A | 3/2010 |

(Continued)

OTHER PUBLICATIONS

International Search Report and Written Opinion of PCT Application No. PCT/JP2020/021968, issued on Aug. 18, 2020, 12 pages of ISRWO.

*Primary Examiner* — Anh Tuan T Nguyen
*Assistant Examiner* — Rynae E Boler
(74) *Attorney, Agent, or Firm* — CHIP LAW GROUP

(57) ABSTRACT

Provided are a medical system, a communication method, an imaging device, an information processing device, and an endoscope system capable of stably transmitting sensor signals output from a sensor that obtains data in a living body by wireless communication. The medical system includes the sensor that is provided in or connected to an insertion part to be inserted into a living body via an insertion aid and obtains the data in the living body, and a sensor communication unit that serves as a communication (Continued)

unit that transmits, by wireless communication, a first sensor signal output from the sensor to an aid communication unit that serves as a communication unit provided in the insertion aid.

23 Claims, 10 Drawing Sheets

(51) Int. Cl.
*H04N 23/50* (2023.01)
*H04N 23/661* (2023.01)

(56) References Cited

U.S. PATENT DOCUMENTS

| | | | |
|---|---|---|---|
| 2003/0004397 | A1 | 1/2003 | Kameya et al. |
| 2008/0195128 | A1 | 8/2008 | Orbay et al. |
| 2008/0312499 | A1 | 12/2008 | Handa et al. |
| 2012/0203082 | A1* | 8/2012 | Livneh ............ A61B 17/00234 600/109 |
| 2013/0245374 | A1* | 9/2013 | Kunz ................ A61B 1/06 600/109 |
| 2014/0002627 | A1* | 1/2014 | Tashiro ............ A61B 8/56 348/71 |
| 2016/0353969 | A1* | 12/2016 | Kikuchi ............ A61B 34/20 |
| 2017/0027425 | A1* | 2/2017 | Mitsuhashi ........ A61B 1/00009 |
| 2017/0117972 | A1* | 4/2017 | Ishibashi ............ H04B 13/005 |
| 2017/0332259 | A1* | 11/2017 | Hirayama ............ H04W 84/18 |

FOREIGN PATENT DOCUMENTS

| | | | | |
|---|---|---|---|---|
| CN | 102802540 | A | | 11/2012 |
| CN | 103476324 | A | | 12/2013 |
| EP | 2114266 | A1 | | 11/2009 |
| EP | 2482736 | A2 | | 8/2012 |
| EP | 2679143 | A1 | | 1/2014 |
| EP | 3217708 | A1 | | 9/2017 |
| JP | 5-154094 | A | | 6/1993 |
| JP | 2003-010112 | A | | 1/2003 |
| JP | 2008-080117 | A | | 4/2008 |
| JP | 2008-307225 | A | | 12/2008 |
| JP | 2010-517704 | A | | 5/2010 |
| JP | 2010-162288 | A | | 7/2010 |
| JP | 2012-245107 | A | | 12/2012 |
| JP | 2013-506491 | A | | 2/2013 |
| JP | 2014-68978 | | * 4/2014 | ............ A61B 1/04 |
| JP | 2014-068987 | A | | 4/2014 |
| KR | 10-2010-0003350 | A | | 1/2010 |
| KR | 10-2012-0103578 | A | | 9/2012 |
| WO | 2008/098251 | A1 | | 8/2008 |
| WO | 2008/098253 | A2 | | 8/2008 |
| WO | 2011/039752 | A2 | | 4/2011 |
| WO | 2013/069691 | A1 | | 5/2013 |
| WO | 2014/054398 | A1 | | 4/2014 |
| WO | 2016/072174 | A1 | | 5/2016 |

* cited by examiner

MEDICAL SYSTEM, COMMUNICATION METHOD, IMAGING DEVICE, INFORMATION PROCESSING DEVICE, AND ENDOSCOPE SYSTEM

CROSS REFERENCE TO RELATED APPLICATIONS

This application is a U.S. National Phase of International Patent Application No. PCT/JP2020/021968 filed on Jun. 3, 2020, which claims priority benefit of Japanese Patent Application No. JP 2019-108699 filed in the Japan Patent Office on Jun. 11, 2019. Each of the above-referenced applications is hereby incorporated herein by reference in its entirety.

TECHNICAL FIELD

The present technology relates to a medical system, a communication method, an imaging device, an information processing device, and an endoscope system, and more particularly, to a medical system, a communication method, an imaging device, an information processing device, and an endoscope system capable of stably transmitting sensor signals from a sensor that obtains data in a living body by wireless communication.

BACKGROUND ART

In recent operation sites, various medical devices are used and power cables and communication cables are arranged everywhere, which hinders movement of medical devices and people. For example, while an endoscope is repeatedly inserted into and removed from the body of a patient for an insertion position change or cleaning, a cable connected to the endoscope may hinder smooth movement of the endoscope.

In view of the above, an endoscope camera that wirelessly transmits image signals has been proposed (e.g., see Patent Document 1).

CITATION LIST

Patent Document

Patent Document 1: Japanese Patent Application Laid-Open No. 2008-80117

SUMMARY OF THE INVENTION

Problems to be Solved by the Invention

Meanwhile, since an image captured by the endoscope camera is used for an operation, it is required to minimize the time from the imaging to the presentation to a user such as a doctor.

However, during the operation, doctors, assistants, nurses, and the like surround, look into, and move around the operative field (operation site) of the patient. Therefore, a transmission path to a device, such as a camera control unit (CCU), which receives image signals may be hindered, and transmission of the image signals may become unstable.

The present technology has been conceived in view of such a situation, and aims to stably transmit sensor signals output from a sensor that obtains data such as an image in a living body by wireless communication.

Solutions to Problems

A medical system according to a first aspect of the present technology includes a sensor that is provided in or connected to an insertion part to be inserted into a living body via an insertion aid and obtains data in the living body, and a sensor communication unit that serves as a communication unit that transmits, by wireless communication, a first sensor signal output from the sensor to an aid communication unit that serves as a communication unit provided in the insertion aid.

A communication method according to a first aspect of the present technology includes transmitting, by wireless communication, a sensor signal output from a sensor that is provided in or connected to an insertion part to be inserted into a living body via an insertion aid and obtains data in the living body to a communication unit provided in the insertion aid.

An imaging device according to a second aspect of the present technology includes an imaging unit that is provided in or connected to an insertion part to be inserted into a living body via an insertion aid and images the inside of the living body, and a sensor communication unit that serves as a communication unit that transmits, by wireless communication, an image signal output from the imaging unit to an aid communication unit that serves as a communication unit provided in the insertion aid.

An information processing device according to a third aspect of the present technology includes a communication unit that receives a sensor signal output from a sensor that is provided in or connected to an insertion part to be inserted into a living body via an insertion aid and obtains data in the living body, and a communication control unit that controls at least one of a communication path or a transmission amount of the sensor signal on the basis of at least one of a communication state or a distance between an aid communication unit that serves as a communication unit provided in the insertion aid and a sensor communication unit that serves as a communication unit that transmits the sensor signal to the aid communication unit by wireless communication.

An endoscope system according to a fourth aspect of the present technology includes an insertion part to be inserted into a living body via an insertion aid, an imaging unit that is provided in or connected to the insertion part and images the inside of the living body, and a sensor communication unit that serves as a communication unit that transmits, by wireless communication, an image signal output from the imaging unit to an aid communication unit that serves as a communication unit provided in the insertion aid.

According to the first aspect of the present technology, a sensor signal output from a sensor that is provided in or connected to an insertion part to be inserted into a living body via an insertion aid and obtains data in the living body is transmitted to a communication unit provided in the insertion aid by wireless communication.

According to the second aspect of the present technology, an image signal output from an imaging unit that is provided in or connected to an insertion part to be inserted into a living body via an insertion aid and images the inside of the living body is transmitted to an aid communication unit that serves as a communication unit provided in the insertion aid by wireless communication.

According to the third aspect of the present technology, a sensor signal output from a sensor that is provided in or connected to an insertion part to be inserted into a living body via an insertion aid and obtains data in the living body is received, and at least one of a communication path or a transmission amount of the sensor signal is controlled on the basis of at least one of a communication state or a distance between an aid communication unit that serves as a communication unit provided in the insertion aid and a sensor communication unit that serves as a communication unit that transmits the sensor signal to the aid communication unit by wireless communication.

According to the fourth aspect of the present technology, an image signal output from an imaging unit that is provided in or connected to an insertion part to be inserted into a living body via an insertion aid and images the inside of the living body is transmitted to an aid communication unit that serves as a communication unit provided in the insertion aid by wireless communication.

MODE FOR CARRYING OUT THE INVENTION

Hereinafter, embodiments for implementing the present technology will be described. Descriptions will be given in the following order.

Figure 1:
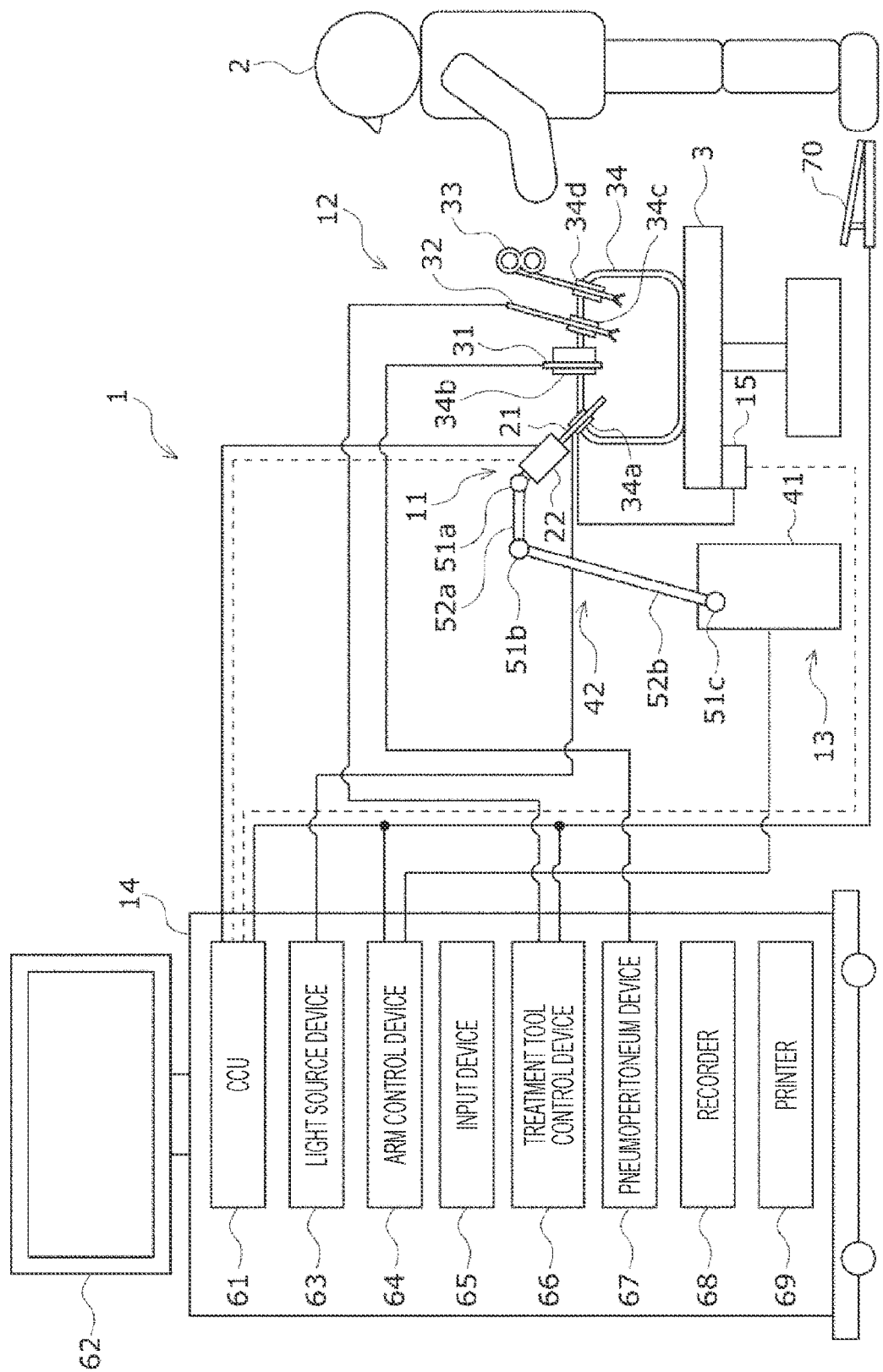
FIG. 1 is a diagram illustrating a first embodiment of a medical system.

1. First Embodiment (First Embodiment of Medical System)
2. Second Embodiment (Second Embodiment of Endoscope and Insertion Aid)
3. Third Embodiment (Second Embodiment of Medical System)
4. Fourth Embodiment (Third Embodiment of Medical System)
5. Variations
6. Others 1. First Embodiment Next, a first embodiment of the present technology will be described with reference to FIGS. 1 to 7.
<Exemplary Configuration of Medical System 1>
FIG. 1 illustrates a first embodiment of a medical system 1 to which the present technology is applied. The medical system 1 constitutes an endoscope system for performing an endoscope operation. This drawing shows an exemplary case where an operator (doctor) 2 performs an endoscope operation on a patient 4 lying on a bed 3 (placed on the bed 3) using the medical system 1.

The medical system 1 includes an endoscope 11, a surgical instrument (surgical tool) 12 other than the endoscope 11, a support arm device 13 that supports the endoscope 11, a cart 14 containing various devices for the endoscope operation, and a communication device 15.

In the endoscope operation, for example, a plurality of tubular insertion aids 34A to 34D called trocars punctures the abdominal wall of the patient 4 instead of a laparotomy for opening the abdominal cavity.

Then, an insertion part 21, which is a lens barrel of the endoscope 11, and other surgical tools 12 are inserted into the body of the patient 4 via the insertion aids 34A to 34D.

Note that, hereinafter, the insertion aids 34A to 34D will be simply referred to as an insertion aid 34 in a case of not being required to distinguish them individually.

The endoscope 11 includes the insertion part 21 and a camera head 22 to be coupled to the base end of the insertion part 21. A portion from the distal end to a certain length of the insertion part 21 is inserted into the body (body cavity) of the patient 4. While this drawing illustrates an exemplary case where the endoscope 11 is configured by what is called a rigid endoscope having the rigid insertion part 21, the endoscope 11 may be configured by what is called a flexible endoscope. Furthermore, the endoscope 11 may be configured by a forward-viewing endoscope, an oblique-viewing endoscope, or a side-viewing endoscope.

An optical system that condenses a subject image using one or a plurality of lenses is provided in the insertion part 21. An opening into which an objective lens is fitted is provided at the distal end of the insertion part 21.

Furthermore, a light source device 63 is coupled to the insertion part 21. The light generated by the light source device 63 is guided to the distal end of the insertion part 21 by a light guide extending inside the insertion part 21, and is emitted toward an object to be observed in the body of the patient 4 via the objective lens.

Figure 2:
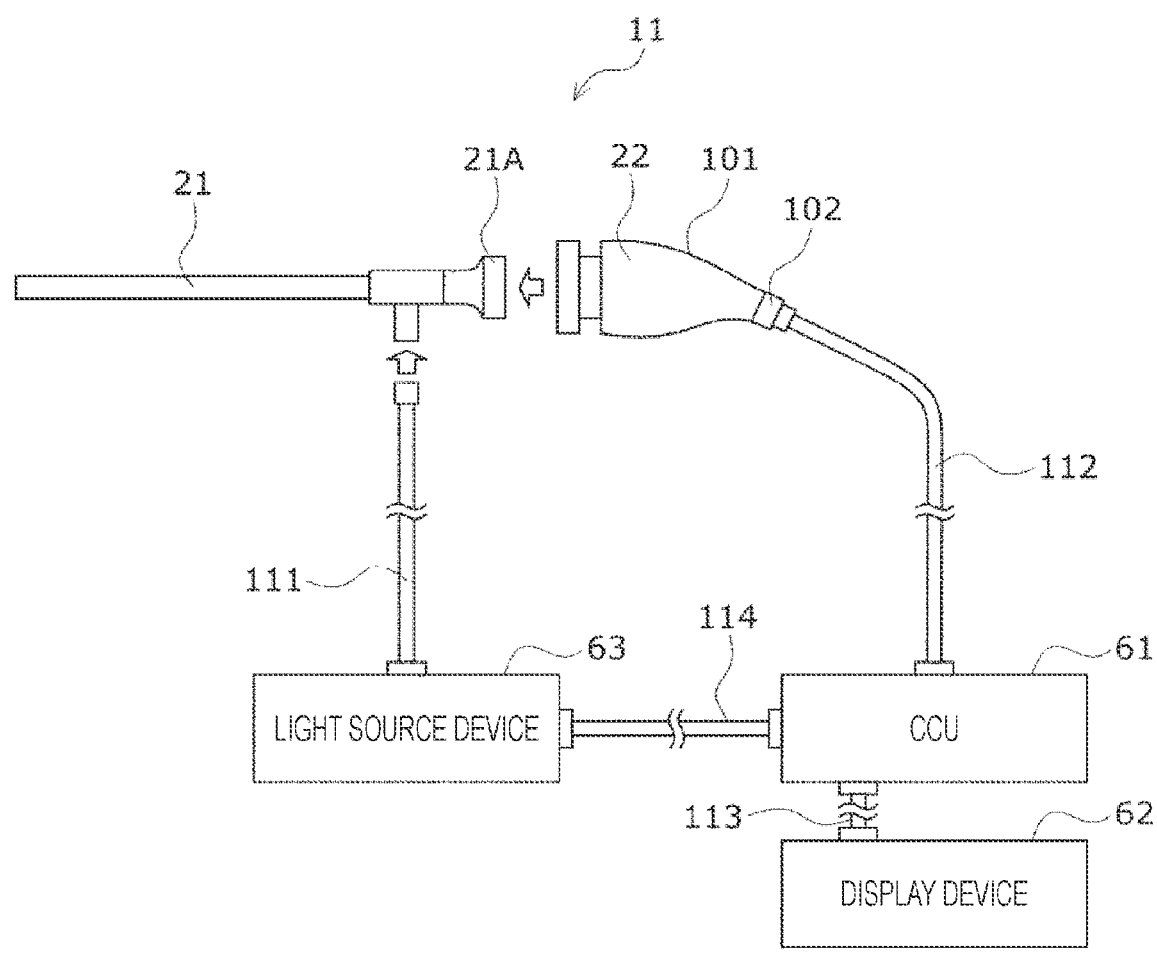
FIG. 2 is a diagram illustrating an exemplary configuration and exemplary connection of an endoscope.

The camera head 22 includes an imaging unit incorporating an optical system, a drive system, and an image sensor, and a communication unit (communication unit 102 in FIG. 2). The optical system typically includes a lens unit, and condenses observation light (reflected light of irradiation light) from a subject taken in from the distal end of the insertion part 21 toward the image sensor. Positions of a zoom lens and a focus lens in the lens unit may be driven and changed by the drive system to variably control imaging conditions such as magnification and a focal length.

The image sensor of the camera head 22 is coupled to the insertion part 21, photoelectrically converts the observation light condensed by the optical system of the insertion part 21, and generates image signals, which are electric signals. That is, the image sensor obtains image data in the body of the patient 4, and generates image signals including the image data. The image sensor may be a three-plate sensor having separate imaging elements that respectively generate image signals of three color components, or may be another type of image sensor such as single-plate type or a double-plate type. The image sensor may include any type of imaging elements such as a complementary metal oxide semiconductor (CMOS) or a charge-coupled device (CCD), for example. The image signals generated by the image sensor are, for example, image signals including RAW data of 4K or more. Note that a part or all of the imaging unit may be provided in the insertion part 21.

The communication unit of the camera head 22 performs wireless communication with (a communication unit provided in) the insertion aid 34, and transmits/receives various signals to/from a camera control unit (CCU) 61 via the insertion aid 34 and the communication device 15. For example, the communication unit of the camera head 22 transmits image signals and the like to the CCU 61 via the insertion aid 34 and the communication device 15, and receives control signals, synchronization signals, clock signals, and the like from the CCU 61. Furthermore, the communication unit of the camera head 22 is capable of directly performing the wireless communication with the CCU 61 without passing through the insertion aid 34 and the communication device 15.

Furthermore, in this example, a pneumoperitoneum tube 31, an energy treatment tool 32, and forceps 33 are illustrated as the other surgical tools 12. The energy treatment tool 32 is used for treatment such as incision or detachment of a tissue, sealing of a blood vessel, or the like based on high-frequency current or ultrasonic vibration. Note that the illustrated surgical tools 12 are merely examples, and other types of surgical tools (e.g., tweezers, a retractor, etc.) may be provided.

An in vivo image of the patient 4 captured by the endoscope 11 is displayed by a display device 62. While viewing the displayed image in real time, the operator 2 performs treatment such as resection of an affected part using the energy treatment tool 32 and the forceps 33, for example. Note that, although illustration is omitted, the pneumoperitoneum tube 31, the energy treatment tool 32, and the forceps 33 are supported by a user, such as the operator 2 or an assistant, during operation.

The support arm device 13 includes an arm part 42 extending from a base part 41. In this example, the arm part 42 includes joint parts 51A to 51C and links 52A and 52B, and supports the endoscope 11. With the arm part 42 driven under control of an arm control device 64, the position and posture of the endoscope 11 are fixed or changed.

The cart 14 stores, for example, the CCU 61, the display device 62, the light source device 63, the arm control device 64, an input device 65, a treatment tool control device 66, a pneumoperitoneum device 67, a recorder 68, and a printer 69.

The CCU 61 includes a processor such as a central processing unit (CPU) and a memory such as a random access memory (RAM), and centrally controls operation of the endoscope 11 and the display device 62. The CCU 61 may further include a frame memory for temporarily storing image signals, and one or more graphics processing unit (GPU) that executes image processing.

The CCU 61 performs various types of image processing on the image signals, and supplies them to the display device 62, the recorder 68, and the like. An image based on a series of image signals output from the CCU 61 may constitute a moving image (video). The image processing executed in the CCU 61 may include general processing such as development and noise reduction, for example.

Furthermore, the CCU 61 is coupled to the camera head 22 via a power cable, and supplies power to the camera head 22. Moreover, the CCU 61 transmits control signals and the like to the camera head 22 via the communication device 15 and the insertion aid 34A to control the camera head 22.

Under the control of the CCU 61, the display device 62 displays a display image based on the image signals from the CCU 61, and outputs sound according to the control signals from the CCU 61.

The light source device 63 includes, for example, a light source corresponding to a light-emitting diode (LED), a xenon lamp, a halogen lamp, a laser light source, or any combination thereof, and supplies irradiation light to be emitted to the object to be observed to the endoscope 11 through the light guide.

The arm control device 64 includes, for example, a processor such as a CPU, and operates according to a predetermined program to control the arm part 42 of the support arm device 13.

The input device 65 includes one or more input interfaces that receive a user input to the medical system 1. The user can input various kinds of information and instructions to the medical system 1 via the input device 65.

The input device 65 may handle any type of user input. For example, the input device 65 may detect physical user input via a mechanism such as a mouse, a keyboard, a switch (e.g., foot switch 70), or a lever. The input device 65 may detect a touch input via a touch panel. The input device 65 may be implemented in a form of a wearable device such as a glasses-like device or a head mounted display (HMD), and may detect a line-of-sight or a gesture of the user. Furthermore, the input device 65 may include a microphone capable of collecting the voice of the user, and may detect a voice command via the microphone.

The treatment tool control device 66 controls the energy treatment tool 32 for treatment such as ablation or incision of a tissue or sealing of a blood vessel.

In order to inflate the body cavity of the patient 4, the pneumoperitoneum device 67 feeds gas into the body cavity via the pneumoperitoneum tube 31 for the purpose of securing a field of view observed by the endoscope 11 and a work space of the operator 2.

The recorder 68 records, in a recording medium, various kinds of information related to medical work (e.g., one or more of setting information, image signals, and measurement information from a vital sensor (not illustrated)), for example.

The printer 69 prints various kinds of information related to medical work in some form such as text, an image, or a graph, for example.

The communication device 15 is provided on the back of the bed 3, more specifically, on the back surface of the floor board of the bed 3. The communication device 15 is coupled to the insertion aid 34A by a communication cable, and performs wired communication with the insertion aid 34A. Furthermore, the communication device 15 performs wireless communication with the CCU 61 to function as a relay between the endoscope 11 and the CCU 61.

Note that various communication schemes can be used for the wireless communication between the camera head 22 and the insertion aid 34 or the CCU 61 and for the wireless communication between the communication device 15 and the CCU 61.

However, since the user (operator 2, etc.) operates the endoscope 11 and the other surgical tools 12 while viewing a display image displayed on the display device 62, it is required to minimize (e.g., within 10 milliseconds) the time from when the inside of the body of the patient 4 is imaged until when the display image is displayed. Furthermore, the image captured by the endoscope 11 has a high resolution (e.g., 4K or more), and the data volume of the image signals is large.

In view of the above, it is preferable to adopt a large-capacity and high-speed communication scheme for the wireless communication between the camera head 22 and the insertion aid 34 or the CCU 61 and for the wireless communication between the communication device 15 and the CCU 61. For example, it is preferable to adopt a communication scheme (e.g., 5G communication scheme) of a wide bandwidth of 6 GHZ or more (millimeter-wave frequency band, etc.).

Meanwhile, as a communication frequency increases with a large-capacity and high-speed communication scheme adopted, rectilinearity of the transmission signals increases. Therefore, the transmission signals are easily blocked by an obstacle, and are hardly transmitted to a distant place.

Meanwhile, with the communication device 15 provided on the back of the bed 3, obstacles between the communication device 15 and the CCU 61 decreases. For example, in a case where the communication device 15 is provided on the bed 3, bodies of doctors, assistants, nurses, and the like serve as obstacles. Meanwhile, in a case where the communication device 15 is provided on the back of the bed 3, legs of doctors, assistants, nurses, and the like serve as obstacles. Since an area of a leg is naturally smaller than that of a body, obstacles between the communication device 15 and the CCU 61 are reduced.

Furthermore, with the communication device 15 provided on the back of the bed 3, it becomes possible to use reflection of the floor for wireless communication.

Therefore, with the communication device 15 provided on the back of the bed 3, the wireless communication between the communication device 15 and the CCU 61 is further stabilized, thereby improving communication quality.

Note that, for example, Wi-Fi (registered trademark), Bluetooth (registered trademark), or the like other than the scheme described above may be adopted as a communication scheme between the camera head 22 and the insertion aid 34, between the camera head 22 and the CCU 61, and between the communication device 15 and the CCU 61.

Furthermore, the communication schemes between the camera head 22 and the insertion aid 34, between the camera head 22 and the CCU 61, and between the communication device 15 and the CCU 61 may or may not be unified.

<Exemplary Configuration and Exemplary Connection of Endoscope 11>

FIG. 2 illustrates an exemplary configuration and exemplary connection of the endoscope 11 in FIG. 1.

The camera head 22 of the endoscope 11 includes a main body 101 and a communication unit 102.

The main body 101 incorporates the imaging unit of the camera head 22. Furthermore, the main body 101 is detachably coupled to an eyepiece 21A at the base end of the insertion part 21.

The communication unit 102 is provided at the rear end of the main body 101, that is, at one end different from one end coupled to the insertion part 21 of the main body 101. The communication unit 102 performs wireless communication with the insertion aid 34A using the communication scheme described above, and transmits/receives image signals, control signals, synchronization signals, clock signals, and the like to/from the CCU 61 via the insertion aid 34A and the communication device 15. Furthermore, the communication unit 102 is capable of directly performing the wireless communication with the CCU 61 without passing through the insertion aid 34A and the communication device 15.

Note that the insertion part 21 and the main body 101 are exposed to high heat and high pressure by sterilization treatment (autoclaving). Accordingly, the main body 101 is usually airtight or includes metal. In view of the above, as in this example, the communication unit 102 is preferably provided outside the main body 101 and at a posterior portion away from the insertion part 21. Furthermore, for example, the communication unit 102 is preferably configured by a detachable component, such as a connector, at a part of the conventional main body 101 to which a communication cable is connected.

One end of a light guide 111 is detachably coupled to the light source device 63, and the other end is detachably coupled to the insertion part 21. In addition, the light guide 111 transmits the irradiation light supplied from the light source device 63 from one end to the other end, and supplies it to the insertion part 21. The irradiation light supplied to the insertion part 21 is emitted from the distal end of the insertion part 21, and is applied to the inside of the living body. The light (subject image) emitted to the inside of the living body and reflected in the living body is condensed by the optical system in the insertion part 21.

One end of a power cable 112 is detachably coupled to the CCU 61 via a connector, and the other end is coupled to the camera head 22 via a connector. In addition, the power cable 112 transmits power output from the CCU 61 to the camera head 22.

One end of a communication cable 113 is detachably coupled to the display device 62, and the other end is detachably coupled to the CCU 61. In addition, the communication cable 113 transmits the image signals processed by the CCU 61 and the control signals output from the CCU 61 to the display device 62.

One end of a communication cable 114 is detachably coupled to the light source device 63, and the other end is detachably coupled to the CCU 61. In addition, the communication cable 114 transmits control signals from the CCU 61 to the light source device 63.

<Exemplary Configuration of Communication Processing Unit 151 of Endoscope 11>

Figure 3:
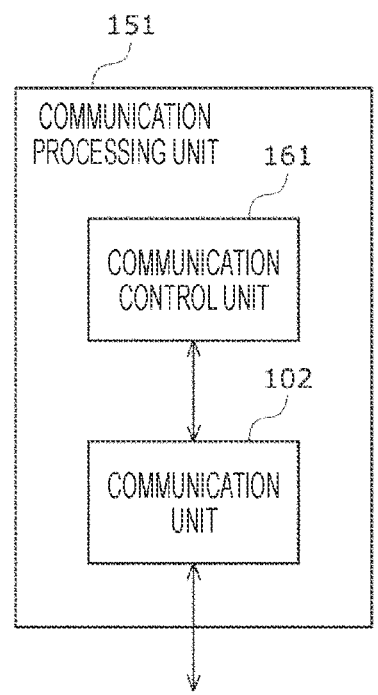
FIG. 3 is a block diagram illustrating an exemplary configuration of a communication processing unit of the endoscope.

FIG. 3 illustrates an exemplary configuration of a communication processing unit 151 that performs processing related to communication of the endoscope 11.

The communication processing unit 151 includes the communication unit 102 described above and a communication control unit 161.

The communication control unit 161 is provided in the main body 101 of the camera head 22, for example, and controls the communication unit 102 to control communication of the endoscope 11. For example, the communication control unit 161 controls a communication path of the communication unit 102 and a transmission amount of signals.

<Exemplary Configuration of Insertion Aid 34A>

Figure 4:
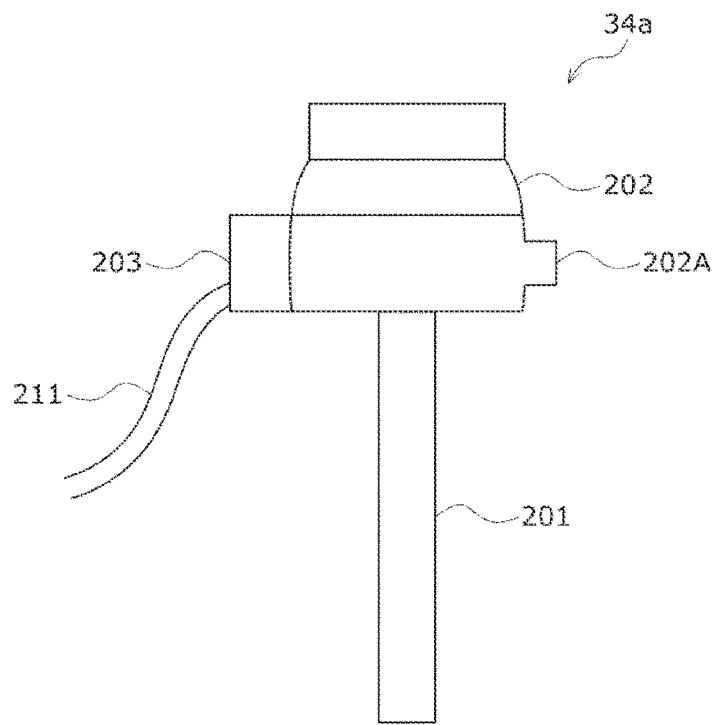
FIG. 4 is a diagram illustrating an exemplary configuration of an appearance of an insertion aid.
Figure 5:
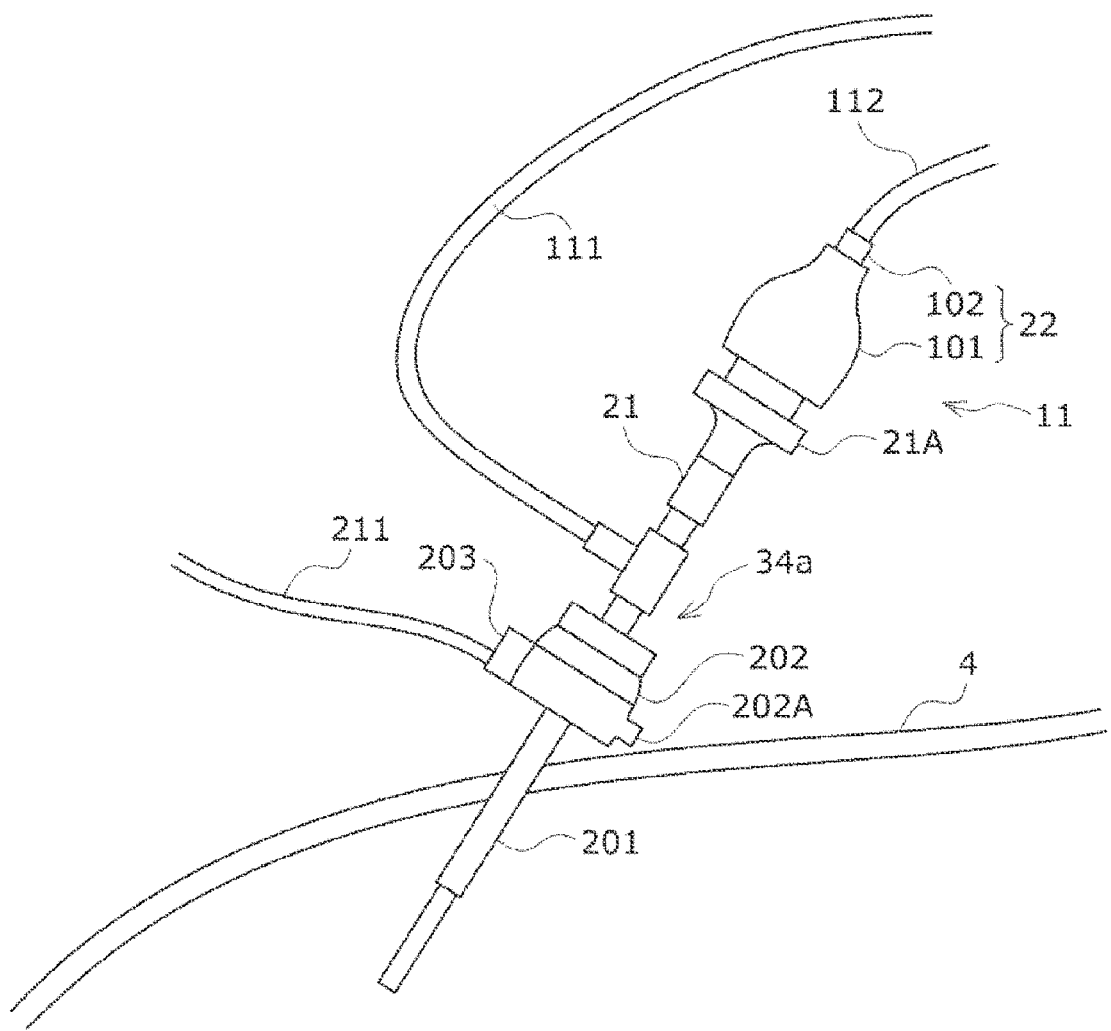
FIG. 5 is a view illustrating exemplary installation of the insertion aid.

FIG. 4 schematically illustrates an exemplary configuration of an appearance of the insertion aid 34A. FIG. 5 schematically illustrates a state in which the patient 4 is punctured by the insertion aid 34A and the insertion part 21 of the endoscope 11 is inserted into the body of the patient 4 via the insertion aid 34A.

The insertion aid 34A includes an insertion part 201, a fixing part 202, and a communication unit 203.

The insertion part 201 is a part to be inserted into the body of the patient 4. That is, the insertion aid 34A is inserted into the body of the patient 4 from the distal end of the insertion part 201.

The fixing part 202 is a part not to be inserted into the body of the patient 4 and to be fixed outside the body. An air supply hole 202A is provided in a side surface of the fixing part 202. The air supply hole 202A is a hole for feeding gas into the body via the insertion part 201, for example.

In addition, as illustrated in FIG. 5, the insertion part 21 of the endoscope 11 is inserted into the body of the patient 4 via the fixing part 202 and the insertion part 201.

The communication unit 203 performs wireless communication with the communication unit 102 of the endoscope 11 using the communication scheme described above. Furthermore, the communication unit 203 is coupled to the communication device 15 on the back of the bed 3 via the communication cable 211, and performs wired communication with the communication device 15.

Note that, if the communication unit 203 is provided in the insertion part 201, for example, the communication unit 203 is to be inserted into the body of the patient 4. In that case, the communication unit 203 may be apart from the communication unit 102 of the endoscope 11, and the body of the patient 4 may serve as an obstacle, which may lead to unstable wireless communication. Therefore, the communication unit 203 is preferably provided on the fixing part 202.

Furthermore, considering that the communication cable 211 is connected, the communication unit 203 is preferably provided on the side surface (outer surface) of the fixing part 202, not on the inner surface (surface facing the insertion part 21) of the fixing part 202.

Moreover, fine vibration is likely to be generated around the inlet and outlet of gas, such as the air supply hole 202A, and the vibration may hinder the wireless communication. In view of the above, the communication unit 203 is preferably provided at a position away from the inlet and outlet of the gas, for example, on the side surface of the fixing part 202, and on the opposite side of the air supply hole 202A.

Furthermore, the communication unit 203 is preferably detachable from the fixing part 202. With this arrangement, it becomes possible to separately perform sterilizing treatment of the main body (insertion part 201 and fixing part 202) and sterilizing treatment of the communication unit 203 of the insertion aid 34A.

Here, the state in which the insertion aid 34A includes the communication unit 203, in other words, the state in which the communication unit 203 is provided in the insertion aid 34A includes not only a state in which the communication unit 203 is in contact with the insertion aid 34A but also a state in which the communication unit 203 is close to the insertion aid 34A. For example, a state in which the communication unit 203 is disposed near the insertion aid 34A by being attached to the surface of the body of the patient 4, for example, is also included.

As described above, the communication unit 102 of the endoscope 11 and the communication unit 203 of the insertion aid 34A are close to each other outside the body of the patient 4, thereby achieving stable wireless communication between them. Furthermore, since wired communication is performed between the communication unit 203 of the insertion aid 34A and the communication device 15, the communication between them is stable. Moreover, as described above, the communication device 15 is provided on the back of the bed 3, thereby achieving stable wireless communication between the communication device 15 and the CCU 61.

Therefore, the communication unit 102 of the endoscope 11 and the CCU 61 can stably perform high-speed communication of large-capacity signals via the communication unit 203 of the insertion aid 34A and the communication device 15. With this arrangement, for example, it becomes possible to promptly and stably transmit the image signals obtained by the endoscope 11 to the CCU 61. As a result, an in vivo image of the patient 4 is promptly and stably displayed on the display device 62, whereby the operator 2 or the like is enabled to continue the operation with security without being interrupted by an abnormality or the like of the displayed image.

Furthermore, the endoscope 11 (camera head 22) is assumed to be held by the user (doctor, etc.) for a long period of time during the operation. Furthermore, even in a case where the endoscope 11 is supported by the support arm device 13, when the camera head 22 increases in size, the support arm device 13 also increases in size. In view of the above, the communication unit 102 to be provided in the endoscope 11 is preferably low-powered (hardly generates heat) and small in size.

Meanwhile, for example, a communication device capable of transmitting/receiving strong wireless signals to/from a device 1 M or more away is large in size and tends to generate heat.

In contrast, since the communication unit 102 of the endoscope 11 and the communication unit 203 of the insertion aid 34A perform wireless communication at close range, it becomes possible to achieve downsizing and low power consumption of the communication device constituting the communication unit 102.

Furthermore, the communication unit 102 of the endoscope 11 and the communication unit 203 of the insertion aid 34A transmit/receive image signals and the like by wireless communication, whereby communication cables of the endoscope 11 can be reduced. Moreover, for example, by wirelessly supplying power to the endoscope 11 to delete the power cable 112, it becomes possible to eliminate the wiring between the endoscope 11 and the CCU 61.

<Exemplary Configuration of Communication Processing Unit 251 of CCU 61>

Figure 6:
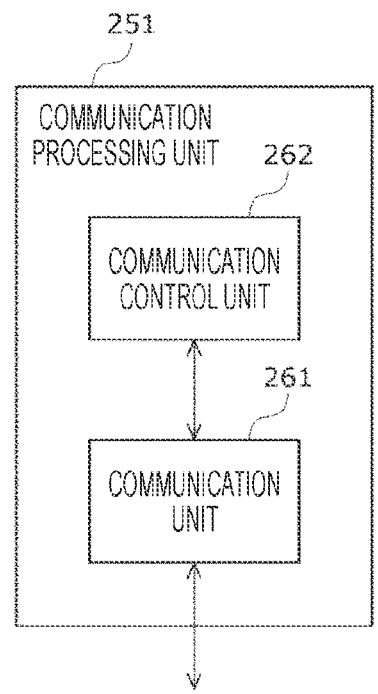
FIG. 6 is a block diagram illustrating an exemplary configuration of a communication processing unit of a CCU.

FIG. 6 illustrates an exemplary configuration of a communication processing unit 251 that performs processing related to communication of the CCU 61.

The communication processing unit 251 includes a communication unit 261 and a communication control unit 262.

The communication unit 261 performs wireless communication with the communication device 15 and the communication unit 102 of the endoscope 11 using the communication scheme described above.

The communication control unit 262 controls the communication unit 261 to control communication of the CCU 61.

<Transmission Amount Control Process>

Figure 7:
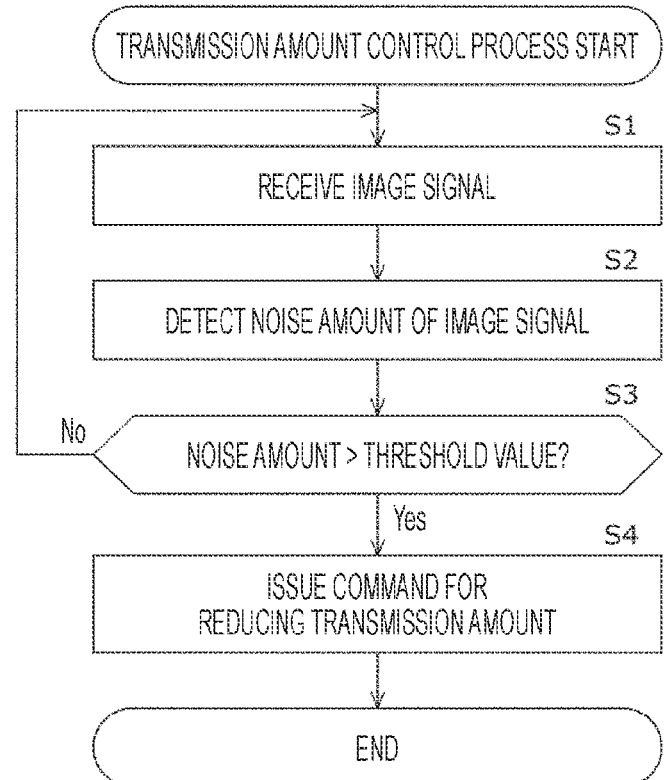
FIG. 7 is a flowchart for explaining a transmission amount control process.

Next, a transmission amount control process to be executed by the CCU 61 will be described with reference to the flowchart of FIG. 7.

In the medical system 1 of FIG. 1, there is a possibility that a display error (e.g., freeze of a displayed image, frame dropping, significant delay, etc.) occurs in the display device 62 due to occurrence of a communication error or packet loss (communication packet loss) between the communication unit 102 of the endoscope 11 and the communication unit 203 of the insertion aid 34A.

Meanwhile, when a display error occurs, it is difficult to confirm an in vivo state of the patient 4, which may delay the operation. In view of the above, even if the image quality is degraded, display images are preferably displayed continuously in real time rather than occurrence of a display error.

Meanwhile, this process is carried out to prevent occurrence of a display error.

Note that this process starts when the power of the CCU 61 is turned on, for example, and ends when it is turned off.

In step S1, the communication unit 261 of the CCU 61 receives image signals transmitted from the communication unit 102 of the endoscope 11 via the communication unit 203 of the insertion aid 34A and the communication device 15. The communication unit 261 supplies the received image signals to the communication control unit 262.

In step S2, the communication control unit 262 detects a noise amount of the image signals. Note that a method of detecting the noise amount is not particularly limited.

In step S3, the communication control unit 262 determines whether or not the noise amount of the image signals has exceeded a predetermined threshold value. In a case where it is determined that the noise amount of the image signals has not exceeded the threshold value, the process returns to step S1.

Thereafter, the process of steps S1 to S3 is repeatedly executed until it is determined in step S3 that the noise amount of the image signals has exceeded the threshold value. That is, imaging and transmission of image signals are continued while the transmission amount of the image signals is in a normal state.

On the other hand, in a case where it is determined in step S3 that the noise amount of the image signals has exceeded the threshold value, the process proceeds to step S4.

In step S4, the communication control unit 262 issues a command for reducing the transmission amount. Specifically, the communication control unit 262 generates command signals for commanding reduction of the transmission amount of the image signals, and transmits them via the communication unit 203.

Meanwhile, the communication unit 102 of the endoscope 11 receives the command signals via the communication device 15 and the communication unit 203 of the insertion aid 34A, and supplies them to the communication control unit 161. The communication control unit 161 instructs the camera head 22 to reduce the data volume of the image signals.

For example, the camera head 22 reduces the resolution of the image from 4K resolution to high definition (HD) (compresses the image), performs crop imaging, or reduces an imaging rate.

With this arrangement, the data volume of the image signals is reduced and the transmission amount of the image signals between the communication unit 102 of the endoscope 11 and the communication unit 203 of the insertion aid 34A is reduced, thereby improving the communication state between them. As a result, display images are stably displayed on the display device 62 in real time so that the user is enabled to confirm the in vivo state in real time, whereby the operation is continued without delay.

Thereafter, the transmission amount control process is terminated.

Note that the transmission amount of the image signals may be switched on the basis of, for example, the number of packet losses or the like other than the noise amount of the image signals.

Furthermore, for example, the communication unit 261 of the CCU 61 may constantly establish communication between the communication unit 102 of the endoscope 11 and the communication unit 203 of the insertion aid 34A, and the communication control unit 262 may monitor the communication state with the endoscope 11 and the insertion aid 34A. Then, the communication control unit 262 may control the communication path or the like on the basis of the communication states of the communication unit 102 and the communication unit 203. For example, in a case where the noise amount or the number of packet losses in the communication with the communication unit 203 of the insertion aid 34A exceeds a predetermined threshold value, or in a case where an abnormality occurs in the communication of the communication unit 203, the communication control unit 262 may perform control in such a manner that the communication unit 261 directly performs wireless communication with the communication unit 102 of the endoscope 11 without passing through the communication unit 203 of the insertion aid 34A and receives image signals.

Moreover, for example, the communication control unit 262 may detect the distance between the communication unit 102 of the endoscope 11 and the communication unit 203 of the insertion aid 34A on the basis of an image based on image signals, a detection result of a distance sensor (not illustrated), or the like, and may control the transmission amount, the communication path, and the like on the basis of the detected distance. For example, in a case where the distance therebetween is equal to or more than a predetermined threshold value, the communication control unit 262 may reduce the transmission amount of the image signals, or may perform control in such a manner that the CCU 61 and the communication unit 102 of the endoscope 11 directly communicate with each other. Meanwhile, for example, in a case where the distance therebetween is less than the predetermined threshold value, the communication control unit 262 may turn back the transmission amount of the image signals to normal, or may perform control in such a manner that the CCU 61 communicates with the communication device 15.

With this arrangement, for example, even when the endoscope 11 is removed from the insertion aid 34A or when the insertion aid 34A is removed from the patient 4 and the endoscope 11 is directly inserted into the body of the patient 4, image signals are stably and continuously supplied to the CCU 61, thereby displaying display images stably and continuously.

Note that, for example, the communication control unit 161 of the endoscope 11 may control the transmission amount, the transmission amount, the communication path, and the like of the image signals by itself on the basis of at least one of the communication state or the distance between the communication unit 102 of the endoscope 11 and the communication unit 203 of the insertion aid 34A, without being instructed by the communication control unit 262 of the CCU 61.

2. Second Embodiment

Next, a second embodiment of the present technology will be described with reference to FIGS. 8 and 9.

While an exemplary case where the endoscope 11 and the insertion aid 34A perform wireless communication outside the body of the patient 4 has been described above, an exemplary case where an endoscope and an insertion aid perform wireless communication inside the body of a patient will be described in the second embodiment.

<Exemplary Configuration of Endoscope 301>

Figure 8:
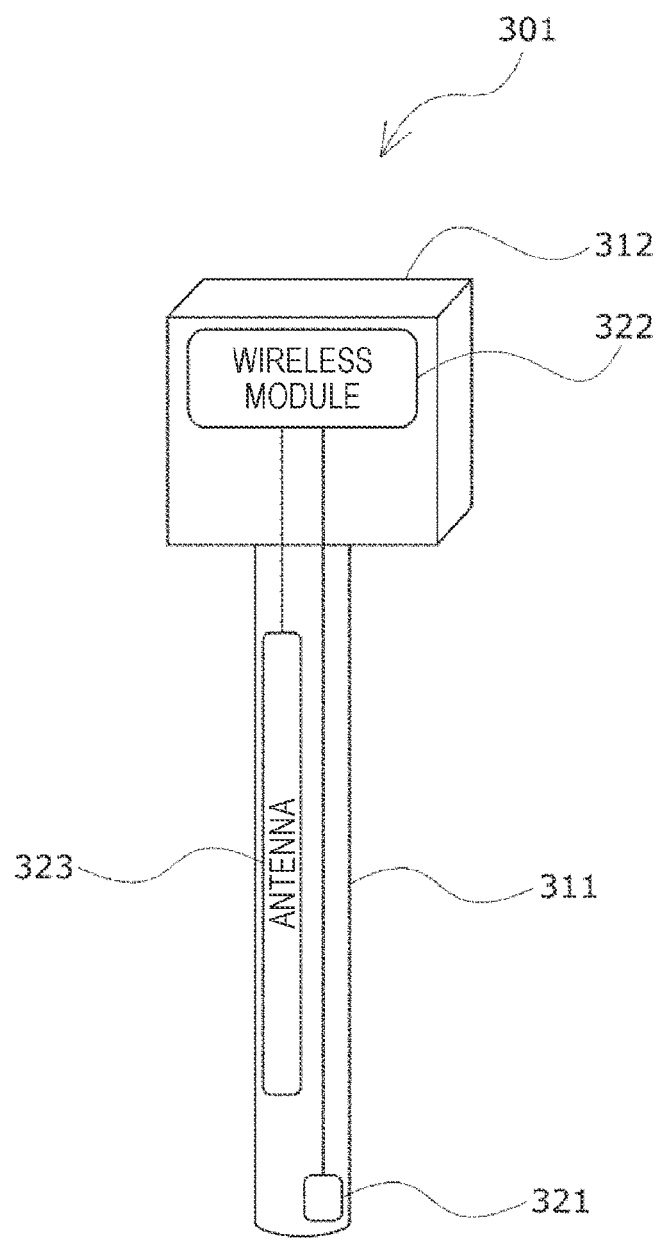
FIG. 8 is a diagram illustrating an exemplary configuration of an endoscope according to a second embodiment.

FIG. 8 schematically illustrates an exemplary configuration of an endoscope 301 to which the present technology is applied.

The endoscope 301 includes an insertion part 311 and an operation unit 312.

The insertion part 311 is rigid or at least partially soft, which has an elongated shape and is inserted into a living body. An image sensor 321 is incorporated in the distal end of the insertion part 311. Furthermore, an antenna 323 is incorporated in the insertion part 311.

The operation unit 312 is a part operated by a user without being inserted into the living body. A wireless module 322 is incorporated in the operation unit 312.

Note that an optical system, such as a lens, may be provided in the insertion part 311, and the image sensor 321 may be provided in the operation unit 312. In addition, the image sensor of the operation unit 312 may photoelectrically convert observation light condensed by the optical system of the insertion part 311 to generate image signals, which are electric signals.

<Exemplary Configuration of Insertion Aid 351>

Figure 9:
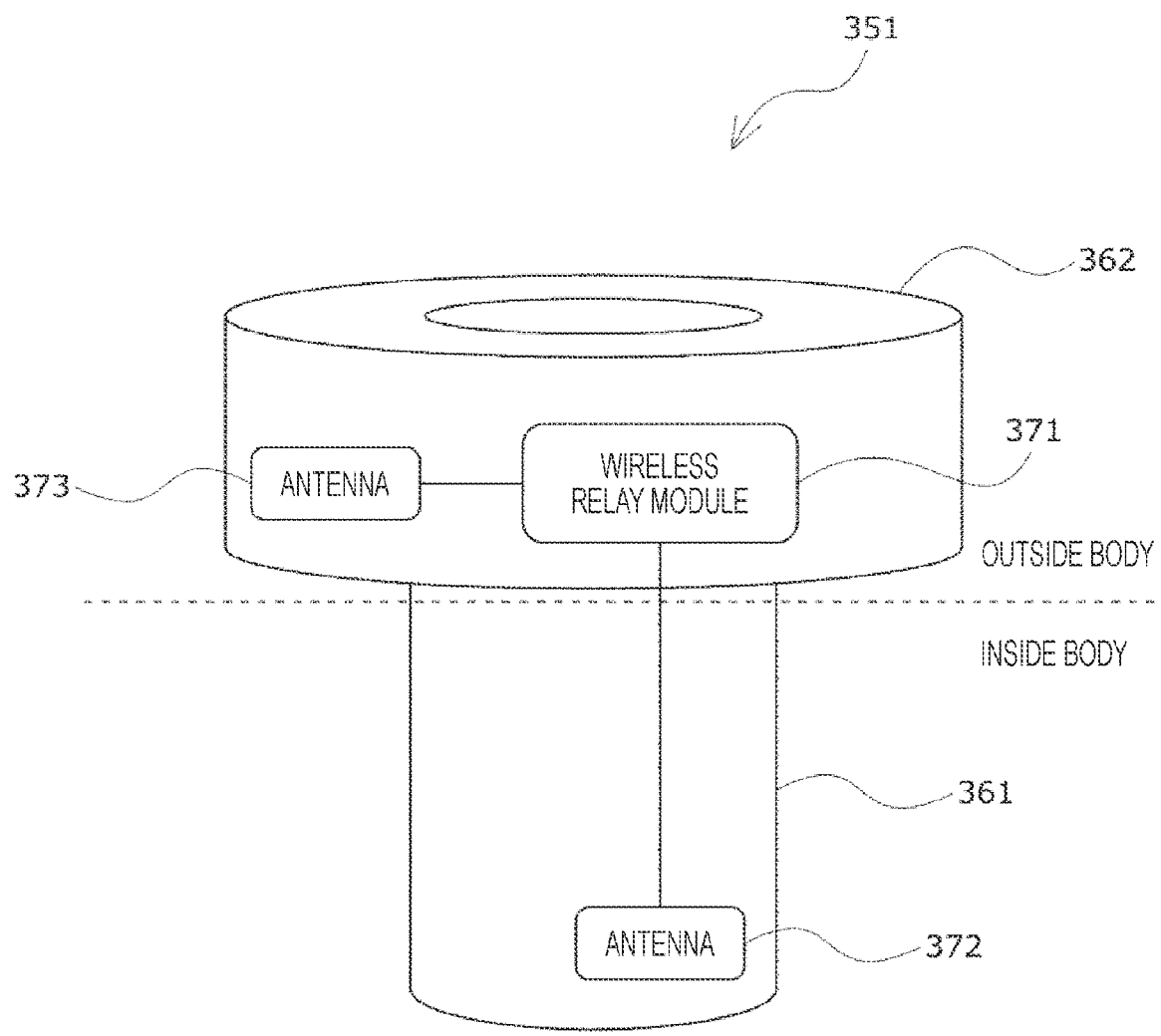
FIG. 9 is a diagram illustrating an exemplary configuration of an insertion aid according to the second embodiment.

FIG. 9 schematically illustrates an exemplary configuration of an insertion aid 351 to which the present technology is applied.

In a similar manner to the insertion aid 34A of FIG. 4, the insertion aid 351 is configured by a trocar including an insertion part 361 and a fixing part 362.

An antenna 372 is incorporated in the insertion part 361.

A wireless relay module 371 and an antenna 373 are incorporated in the fixing part 362.

In addition, the wireless relay module 371 relays a communication network inside the living body and a communication network outside the living body. The communication network inside the living body includes, for example, the wireless module 322 and the antenna 323 of the endoscope 301, the wireless relay module 371 and the antenna 372 of the insertion aid 351, and the like. The communication network outside the living body includes, for example, the wireless relay module 371 and the antenna 373 of the insertion aid 351, a communication device 15, a communication unit 261 of a CCU 61, and the like.

For example, the image sensor 321 of the endoscope 301 captures an in vivo image, and supplies the obtained image signals to the wireless module 322. In the living body, the wireless module 322 transmits the image signals to the insertion aid 351 via the antenna 323.

The wireless relay module 371 of the insertion aid 351 receives the image signals via the antenna 372. At this time, the antenna 323, the insertion aid 351, and the antenna 372 of the endoscope 301 are close to each other in the living body, whereby the image signals are stably transmitted in the living body.

The wireless relay module 371 transmits the image signals via the antenna 373. The image signals transmitted from the antenna 373 are received by, for example, the communication device 15 or the communication unit 261 of the CCU 61.

Note that the wireless relay module 371 is also capable of receiving, via the antenna 372, sensor signals transmitted from a device other than the endoscope 301 in the living body. For example, the wireless relay module 371 is capable of receiving, via the antenna 372, image signals transmitted from a capsule endoscope (not illustrated) inserted into the living body.

Then, for example, the wireless relay module 371 can synchronize the image signals from the endoscope 301 and the image signals from the capsule endoscope by adding a time stamp to both of them. For example, the CCU 61 can cause the display device 62 to display an image based on the image signals of the endoscope 301 and an image based on the image signals of the capsule endoscope in synchronization with each other on the basis of the added time stamp.

3. Third Embodiment

Next, a third embodiment of the present technology will be described with reference to FIG. 10.

Figure 10:
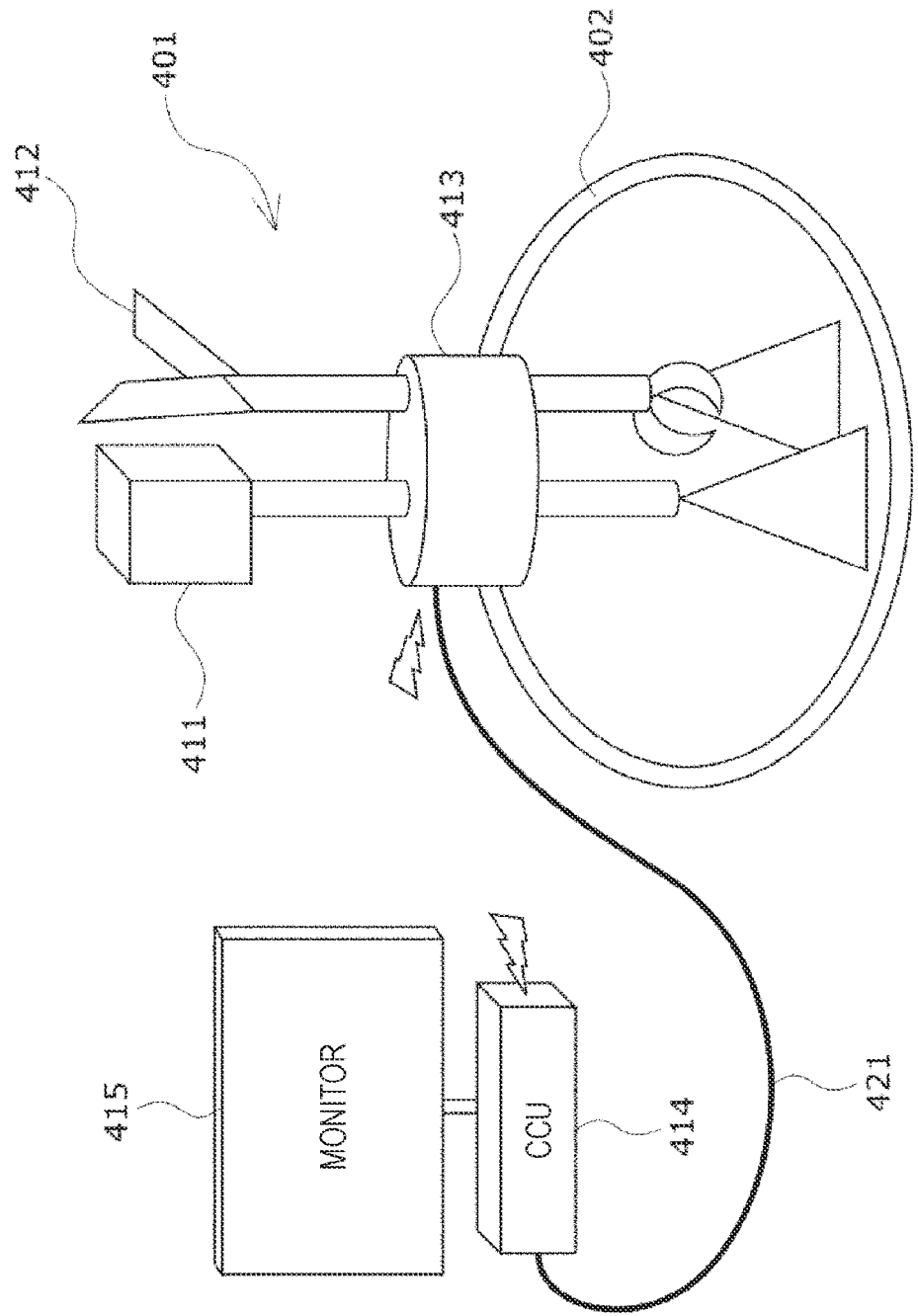
FIG. 10 is a block diagram illustrating a medical system according to the second embodiment.

FIG. 10 illustrates an exemplary configuration of a medical system 401 to which the present technology is applied.

The medical system 401 includes an endoscope 411, a camera-equipped treatment tool 412, an insertion aid 413, a CCU 414, and a monitor 415. The endoscope 411 and the camera-equipped treatment tool 412 are inserted into the living body of a patient 402 via the insertion aid 413. The insertion aid 413 is coupled to the CCU 414 via a communication cable 421.

The endoscope 411 captures an in vivo image of the patient 402. Furthermore, in a similar manner to the endoscope 301 of FIG. 8, the endoscope 411 includes a communication unit (not illustrated) that performs wireless communication, and performs wireless communication with (a communication unit (not illustrated) provided in) the insertion aid 413 in the living body of the patient 402. For example, the endoscope 411 transmits, to the insertion aid 413, image signals obtained by capturing an in vivo image of the patient 402.

The camera-equipped treatment tool 412 is a surgical tool to be used for an operation, which includes a camera and is capable of capturing an in vivo image of the patient 402. Furthermore, in a similar manner to the endoscope 411, the camera-equipped treatment tool 412 includes a communication unit (not illustrated) that performs wireless communication, and performs wireless communication with (a communication unit (not illustrated) provided in) the insertion aid 413 in the living body of the patient 402. For example, the camera-equipped treatment tool 412 transmits, to the insertion aid 413, image signals obtained by capturing an in vivo image of the patient 402.

The insertion aid 413 has a communication function, and relays a communication network inside the living body and a communication network outside the living body in a similar manner to the insertion aid 351 of FIG. 9. The communication network inside the living body includes, for example, the endoscope 411, the camera-equipped treatment tool 412, and the insertion aid 413. The communication network outside the living body includes, for example, the insertion aid 413 and the CCU 414.

For example, the insertion aid 413 transmits, to the CCU 414, the image signals received from the endoscope 411 and the camera-equipped treatment tool 412. For example, the insertion aid 413 receives control signals transmitted from the CCU 414, and transmits them to the endoscope 411 and to the camera-equipped treatment tool 412.

Furthermore, for example, inside the living body of the patient 402, the insertion aid 413 relates the communication between the endoscope 411 and the camera-equipped treatment tool 412.

Moreover, for example, the insertion aid 413 is capable of synchronizing the image signals received from the endoscope 411 and the image signals received from the camera-equipped treatment tool 412 by adding a time stamp to both of them. For example, the CCU 414 can cause the monitor 415 to display an image based on the image signals of the endoscope 411 and an image based on the image signals of the camera-equipped treatment tool 412 in synchronization with each other on the basis of the added time stamp.

Note that the insertion aid 413 and the CCU 414 may wirelessly communicates with each other without being connected by the communication cable 421.

As described above, the endoscope 411 and the camera-equipped treatment tool 412 are inserted into the body of the patient 402 via one insertion aid 413 and perform wireless communication with the insertion aid 413, whereby it becomes possible to reduce the number of the insertion aids 413.

Furthermore, it becomes possible to smoothly perform communication in the communication network inside the living body, communication network in the communication network outside the living body, and relay between the communication network inside the living body and the communication network outside the living body via the insertion aid 413.

4. Fourth Embodiment

Next, a fourth embodiment of the present technology will be described with reference to FIG. 11.

Figure 11:
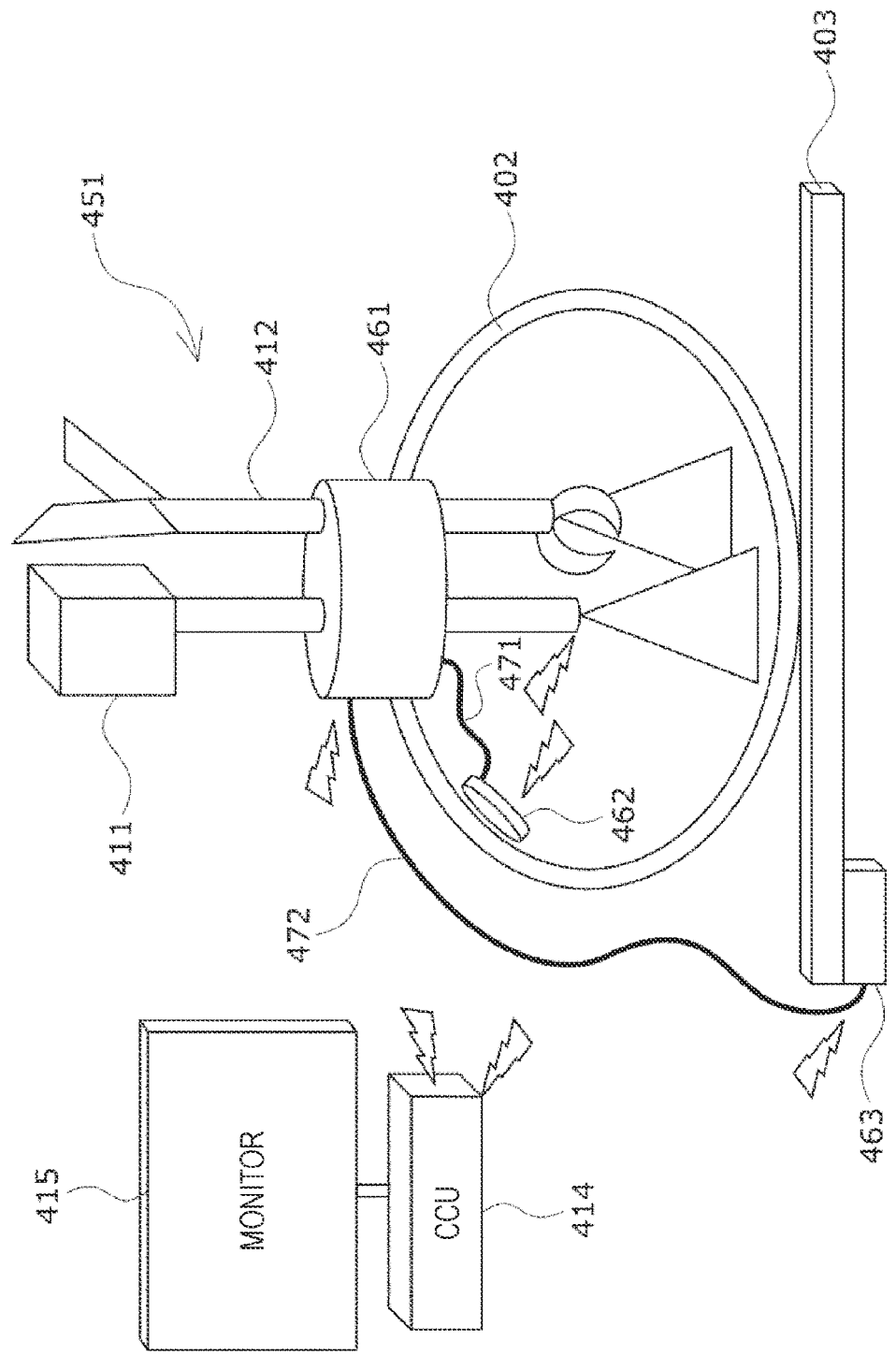
FIG. 11 is a block diagram illustrating a medical system according to a third embodiment.

FIG. 11 illustrates an exemplary configuration of a medical system 451 to which the present technology is applied. Note that, in the drawing, a part corresponding to that of the medical system 401 of FIG. 10 is denoted by the same reference sign, and descriptions thereof will be omitted as appropriate.

The medical system 451 is the same as the medical system 401 in that it includes an endoscope 411, a camera-equipped treatment tool 412, a CCU 414, and a monitor 415, and is different in that it includes an insertion aid 461 instead of the insertion aid 413 and includes an antenna 462 and a wireless relay 463.

The endoscope 411 and the camera-equipped treatment tool 412 are inserted into the body of a patient 402 via the insertion aid 461. The antenna 462 is set in the body of the patient 402, and is coupled to the insertion aid 461 via a communication cable 471. The wireless relay 463 is provided on the back of a bed 403 on which the patient 402 lies. Furthermore, the wireless relay 463 is coupled to the insertion aid 461 via a communication cable 472. Therefore, the antenna 462 and the wireless relay 463 are coupled to each other via the communication cable 471, the insertion aid 461, and the communication cable 472.

The insertion aid 461 has a communication function, and relays a communication network inside the living body and a communication network outside the living body in a similar manner to the insertion aid 461 of FIG. 10. The communication network inside the living body includes, for example, the endoscope 411, the camera-equipped treatment tool 412, the insertion aid 461, and the antenna 462. The communication network outside the living body includes, for example, the insertion aid 461, the wireless relay 463, and the CCU 414.

In addition, the endoscope 411, the camera-equipped treatment tool 412, and the CCU 414 communicate with each other via the antenna 462, the communication cable 471, the insertion aid 461, the communication cable 472, and the wireless relay 463. Furthermore, the endoscope 411 and the camera-equipped treatment tool 412 communicate with each other via the antenna 462 and the insertion aid 461.

Note that, for example, the antenna 462, the communication cable 471, and the communication cable 472 may be detachable from the insertion aid 461.

Furthermore, for example, an existing insertion aid may be used as a wireless relay with the antenna 462, the communication cable 471, and the communication cable 472 attached to the existing insertion aid.

5. Variations

Hereinafter, variations of the above-described embodiments according to the present technology will be described.
<Variation for Communication Device 15>

For example, in the medical system 1 of FIG. 1, a plurality of communication devices 15 may be provided. In this case, for example, the plurality of communication devices 15 communicate with each other by wire or wirelessly. Furthermore, each of the communication devices 15 is coupled to the insertion aid 34A by wire, or one communication device 15 is coupled to the insertion aid 34A by wire. Moreover, each of the communication devices 15 performs wireless communication with the CCU 61.

Then, for example, the communication device 15 with the best communication state with the CCU 61 among the plurality of communication devices 15 transmits image signals received from the endoscope 11 to the CCU 61 via the insertion aid 34A.

Note that the communication device 15 with the best communication state is, for example, the communication device 15 with the most stable communication speed with the CCU 61, the communication device 15 with the least packet loss with the CCU 61, the communication device 15 with the maximum signal strength with the CCU 61, or the like.

With this arrangement, it becomes possible to further improve the communication state between the communication device 15 and the CCU 61.
<Variation for Insertion Aid 34>

While an exemplary case where only the insertion aid 34A includes the communication unit 203 has been described in the first embodiment above, a plurality of insertion aids 34 may include a communication unit to allow them to perform wireless communication with the communication unit 102 of the endoscope 11. In this case, the plurality of insertion aids 34 may share the communication device 15, or the communication device 15 may be individually provided for each of the insertion aids 34.

In addition, for example, the communication control unit 161 of the endoscope 11 may select the optimum insertion aid 34 to transmit image signals. For example, the communication control unit 161 selects the insertion aid 34 including a communication unit having the shortest distance to the communication unit 102 or the insertion aid 34 including a communication unit having the best communication state with the communication unit 102, and transmits image signals. Note that the communication control unit 161 may switch the insertion aid 34 for transmitting image signals as needed depending on the communication state.

Furthermore, for example, the communication control unit 161 of the endoscope 11 may perform control to communicate with the communication unit of the insertion aid 34 set in advance. For example, the communication control unit 161 causes each of the insertion aids 34 to broadcast endoscope ID for identifying the endoscope 11 from the communication unit 102. Then, among the insertion aids 34 that have received the endoscope ID, the communication unit of the insertion aid 34 in which the endoscope ID set in advance by the CCU 61 matches the endoscope ID received from the endoscope 11 may communicate with the communication unit 102 of the endoscope 11.

Moreover, for example, the communication unit 102 of the endoscope 11 may transmit the endoscope ID to the CCU 61, and the communication unit 203 of each of the insertion aids 34 may transmit insertion aid ID for identifying each of the insertion aids 34 to the CCU 61. In addition, for example, the display device 62 may display, on the operation screen, the endoscope ID and the insertion aid ID received by the CCU 61, and the user may select a pair of the insertion aid 34 and the endoscope 11 for performing wireless communication while viewing the operation screen.

Furthermore, for example, the communication unit 102 of the endoscope 11 may transmit image signals to the communication units of the plurality of insertion aids 34. In this case, for example, the communication unit of the insertion aid 34 with the least packet loss of the received image signals may transmit the image signals to the communication device 15. Alternatively, the communication device 15 may transmit, to the CCU 61, the image signals with the least packet loss from among the image signals received from the communication units of the plurality of insertion aids 34.

Moreover, for example, the communication unit of each of the insertion aids 34 may share the packets of the image signals received from the endoscope 11 and transmit them to the CCU 61 via the communication device 15. In this case, for example, the communication control unit 262 of the CCU 61 restores the image signals by combining the packets transmitted from the communication units of the respective insertion aids 34. Furthermore, for example, in a case where packet loss occurs in signals received from a communication unit of a certain insertion aid 34, the communication control unit 262 may complement the signals with signals received from a communication unit of another insertion aid 34.

<Variation for Communication Scheme>

For example, the communication device 15 may be provided at a position in contact with the body of the patient 4, and the communication unit 203 of the insertion aid 34A and the communication device 15 may communicate with each other using human body communication (body area network) in which communication is performed by applying a current to the body surface of the patient 4. With this arrangement, it becomes possible to reduce the communication cables between the insertion aid 34A and the communication device 15. Furthermore, it becomes possible to transmit a large volume of data without a cable between the insertion aid 34A (sanitary area) and the communication device 15 on the bed 3 (insanitary area), whereby the sanitary conditions around the surgical site of the patient 4 can be maintained.

Furthermore, for example, the human body communication may be performed between the communication units of the plurality of insertion aids 34.

Moreover, for example, a connecting part of a communication cable (e.g., connector, jack, etc.) may be provided on the camera head 22 of the endoscope 11 so that the communication unit 102 is also enabled to perform wired communication. In addition, for example, in a case where an abnormality occurs in wireless communication between the communication unit 102 of the endoscope 11 and the communication unit 203 of the insertion aid 34, the endoscope 11 and the CCU 61 may be coupled to each other by a cable, and the communication unit 102 may transmit image signals to the CCU 61 by wired communication. With this arrangement, even in a case where abnormality occurs in the wireless communication, display images can be continuously displayed, whereby it becomes possible to avoid interruption of the operation.

Furthermore, for example, a communication cable may be provided in the power cable 112, and lower-capacity signals such as control signals may be transmitted between the endoscope 11 and the CCU 61 via the communication cable in the power cable 112.

Moreover, for example, the communication device 15 and the CCU 61 may be coupled to each other by a communication cable to perform wired communication between them.

Furthermore, for example, the communication unit 203 of the insertion aid 34A and the CCU 61 may directly communicate with each other without the communication device 15 provided. In this case, although the communication unit 203 and the CCU 61 preferably perform wireless communication, the communication unit 203 and the CCU 61 may be coupled to each other by a communication cable to perform wired communication with each other.

<Other Variations>

Although an exemplary case where the image signals are transmitted via the communication unit 203 of the insertion aid 34A has been described above, the signals to be transmitted using the present technology are not limited to the image signals. For example, sensor signals including in vivo data detected by various sensors provided at the distal end of the surgical tool 12 may be transmitted to the CCU 61 via the communication unit 203 of the insertion aid 34A and the communication device 15. Examples of such sensors include a time of flight (TOF) sensor, a vital sensor, a distance sensor, and a temperature sensor.

Furthermore, the endoscope or the surgical tool may be inserted into the living body from a natural hole such as a nasal cavity via the insertion aid.

Moreover, the endoscope or the surgical tool may be inserted into the living body from a natural hole without passing through the insertion aid. In this case, for example, sensor signals such as image signals are transmitted via a communication unit of an insertion aid used to insert another endoscope or surgical tool near the endoscope or surgical tool.

6. Others

<Exemplary Computer Configuration>

The series of processing described above may be executed by hardware or by software. In a case where the series of processing is executed by software, a program constituting the software is installed in a computer. Here, examples of the computer include a computer incorporated in dedicated hardware, a general-purpose personal computer capable of implementing various functions by installing various programs, and the like.

Figure 12:
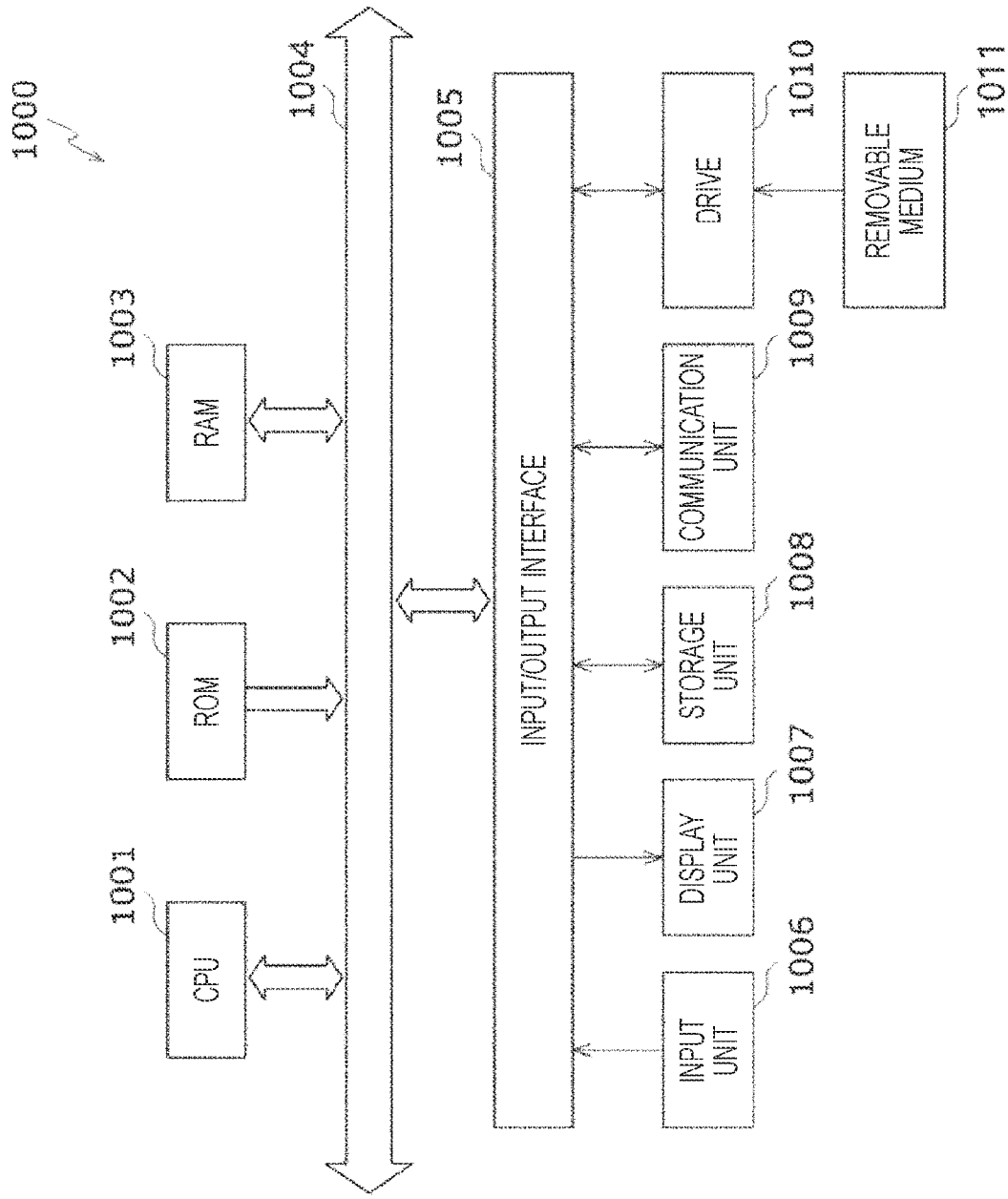
FIG. 12 is a diagram illustrating an exemplary configuration of a computer.

FIG. 12 is a block diagram illustrating an exemplary hardware configuration of a computer that executes, using a program, the series of processing described above.

In the computer, a central processing unit (CPU) 1001, a read only memory (ROM) 1002, and a random access memory (RAM) 1003 are coupled to one another via a bus 1004.

An input/output interface 1005 is further connected to the bus 1004. An input unit 1006, an output unit 1007, a storage unit 1008, a communication unit 1009, and a drive 1010 are coupled to the input/output interface 1005.

The input unit 1006 includes a keyboard, a mouse, a microphone, and the like. The output unit 1007 includes a display, a speaker, and the like. The storage unit 1008 includes a hard disk, a non-volatile memory, and the like. The communication unit 1009 includes a network interface and the like. The drive 1010 drives a removable medium 1011 such as a magnetic disk, an optical disk, a magneto-optical disk, or a semiconductor memory.

In the computer configured as described above, for example, the CPU 1001 loads the program stored in the storage unit 1008 into the RAM 1003 via the input/output interface 1005 and the bus 1004 and executes the program, thereby performing the series of processing described above.

The program to be executed by the computer (CPU 1001) may be provided by, for example, being recorded in the removable medium 1011 as a package medium or the like. Furthermore, the program may be provided through a wired or wireless transmission medium such as a local area network, the Internet, or digital satellite broadcasting.

In the computer, the program may be installed in the storage unit 1008 via the input/output interface 1005 by attaching the removable medium 1011 to the drive 1010. Furthermore, the program may be received by the communication unit 1009 via a wired or wireless transmission medium and installed in the storage unit 1008. In addition, the program may be installed in the ROM 1002 or the storage unit 1008 in advance.

Note that the program to be executed by the computer may be a program in which processing is executed in a time-series manner according to the order described in the present specification, or may be a program in which processing is executed in parallel or at a necessary timing such as when a call is made.

Furthermore, in the present specification, a system indicates a set of a plurality of constituent elements (devices, modules (parts), etc.), and it does not matter whether or not all the constituent elements are in the same housing. Therefore, a plurality of devices housed in separate housings and connected through a network, and one device in which a plurality of modules is housed in one housing are both systems.

Note that an embodiment of the present technology is not limited to the embodiments described above, and various modifications can be made without departing from the gist of the present technology.

For example, the present technology may employ a configuration of cloud computing in which one function is shared and jointly processed by a plurality of devices via a network.

Furthermore, each step described in the flowchart described above may be executed by one device or shared by a plurality of devices.

Moreover, in a case where a plurality of processes is included in one step, the plurality of processes included in the one step may be executed by one device or shared by a plurality of devices.

<Exemplary Configuration Combination>

The present technology may also employ the following configurations.

(1)

A medical system including:
 a sensor that is provided in or connected to an insertion part to be inserted into a living body via an insertion aid and obtains data in the living body; and
 a sensor communication unit that serves as a communication unit that transmits, by wireless communication, a first sensor signal output from the sensor to an aid communication unit that serves as a communication unit provided in the insertion aid.

(2)

The medical system according to (1) described above, further including:
 a communication control unit that selects a communication path of the first sensor signal on the basis of at least one of a communication state or a distance with the aid communication unit.

(3)

The medical system according to (2) described above, in which
 the communication path of the first sensor signal includes a first communication path that passes through the aid communication unit and a second communication path that does not pass through the aid communication unit.

(4)

The medical system according to (1) described above, further including:
 a communication control unit that controls a transmission amount of the first sensor signal on the basis of a communication state with the aid communication unit.

(5)

The medical system according to (1) described above, in which
 the sensor communication unit performs wireless communication with a plurality of the aid communication units respectively provided in a plurality of the insertion aids inserted into the living body.

(6)

The medical system according to (5) described above, further including:
 a communication control unit that selects the aid communication unit with which the sensor communication unit performs the wireless communication from among the plurality of aid communication units.

(7)

The medical system according to (6) described above, in which
 the communication control unit selects the aid communication unit with which the sensor communication unit performs the wireless communication on the basis of at least one of a communication state or a distance with each of the aid communication units.

(8)

The medical system according to (6) or (7) described above, in which
 the sensor communication unit transmits the first sensor signal to each of the aid communication units.

(9)

The medical system according to any one of (1) to (8) described above, in which
 the sensor communication unit performs wireless communication with the aid communication unit in the living body via an antenna provided in the insertion part.

(10)

The medical system according to (9) described above, in which
 the sensor communication unit communicates with a communication unit provided in a surgical tool inserted into the living body via the aid communication unit in the living body.

(11)

The medical system according to any one of (1) to (11) described above, further including:
 an endoscope including:
 the insertion part;
 an imaging unit including an image sensor serving as the sensor; and
 the sensor communication unit.

(12)

The medical system according to (11) described above, in which
 the endoscope further includes:
 a connection part capable of being connected to a communication cable, and
 the sensor communication unit is capable of performing wired communication with an information processing device that uses the first sensor signal via the communication cable.

(13)

The medical system according to any one of (1) to (12) described above, in which the sensor communication unit performs communication using a frequency of a millimeter-wave frequency band.

(14)

The medical system according to any one of (1) to (13) described above, further including:

the insertion aid.

(15)

The medical system according to (14) described above, in which the aid communication unit relays a first communication network configured inside the living body and a second communication network configured outside the living body.

(16)

The medical system according to (15) described above, in which the insertion aid further includes:

a first antenna provided at a part to be inserted into the living body, and the aid communication unit performs wireless communication with the sensor communication unit via the first antenna.

(17)

The medical system according to (16) described above, in which the insertion aid further includes:

a second antenna provided at a part not to be inserted into the living body, and the aid communication unit performs communication in the second communication network via the second antenna.

(18)

The medical system according to any one of (14) to (17) described above, in which the aid communication unit performs wired communication with a communication device that transmits the first sensor signal to an information processing device via a communication cable.

(19)

The medical system according to (18) described above, in which the communication device is provided on a bed on which the living body is placed.

(20)

The medical system according to (14) described above, in which the aid communication unit performs human body communication with a communication device in contact with the living body or with another aid communication unit provided in another insertion aid via the living body.

(21)

The medical system according to any one of (14) to (20) described above, in which the aid communication unit adds a time stamp to the first sensor signal received from the sensor communication unit and to a second sensor signal received from another surgical tool.

(22)

The medical system according to any one of (12) to (21) described above, in which the aid communication unit is detachable from the insertion aid.

(23)

A communication method including:

transmitting, by wireless communication, a sensor signal output from a sensor that is provided in or connected to an insertion part to be inserted into a living body via an insertion aid and obtains data in the living body to a communication unit provided in the insertion aid.

(24)

An imaging device including:

an imaging unit that is provided in or connected to an insertion part to be inserted into a living body via an insertion aid and images the inside of the living body; and a sensor communication unit that serves as a communication unit that transmits, by wireless communication, an image signal output from the imaging unit to an aid communication unit that serves as a communication unit provided in the insertion aid.

(25)

An information processing device including:

a communication unit that receives a sensor signal output from a sensor that is provided in or connected to an insertion part to be inserted into a living body via an insertion aid and obtains data in the living body; and a communication control unit that controls at least one of a communication path or a transmission amount of the sensor signal on the basis of at least one of a communication state or a distance between an aid communication unit that serves as a communication unit provided in the insertion aid and a sensor communication unit that serves as a communication unit that transmits the sensor signal to the aid communication unit by wireless communication.

(26)

An endoscope system including:

an insertion part to be inserted into a living body via an insertion aid;

an imaging unit that is provided in or connected to the insertion part and images the inside of the living body; and a sensor communication unit that serves as a communication unit that transmits, by wireless communication, an image signal output from the imaging unit to an aid communication unit that serves as a communication unit provided in the insertion aid.

Note that the effects described herein are merely examples and not limited, and additional effects may be included.

REFERENCE SIGNS LIST

1 Medical system
3 Bed
11 Endoscope
12 Surgical tool
15 Communication device
21 Insertion part
22 Camera head
34A to 34D Insertion aid
62 Display device
101 Main body
102 Communication unit
151 Communication processing unit
161 Communication control unit
201 Insertion part
202 Fixing part
202A Air supply hole
203 Communication unit 251 Communication processing unit
261 Communication unit
262 Communication control unit
301 Endoscope
311 Insertion part
312 Operation unit
321 Image sensor
322 Wireless module
323 Antenna
351 Insertion aid
361 Insertion part
362 Fixing part
371 Wireless relay module
372, 373 Antenna
401 Medical system
403 Bed
411 Endoscope
412 Camera-equipped treatment tool
413 Insertion aid
414 CCU
421 Communication cable
451 Medical system
461 Insertion aid
462 Antenna
463 Wireless relay
471, 472 Communication cable

The invention claimed is:

1. A medical system, comprising:
a first insertion aid that includes a first communication circuit; and
an endoscope that includes:
an insertion part insertable into a living body via the first insertion aid;
a sensor that is one of inside the insertion part or connectable to the insertion part,
wherein the sensor is configured to:
obtain data related to the living body; and
output a first sensor signal that includes the data;
a second communication circuit; and
a central processing unit (CPU) configured to select a communication path of the first sensor signal from a first communication path that passes through the first communication circuit and a second communication path that does not pass through the first communication circuit, wherein
the selection of the communication path is based on at least one of
a communication state between the first communication circuit and the second communication circuit, or
a distance between the first communication circuit and the second communication circuit, and
the second communication circuit is configured to transmit, based on the selected communication path, the first sensor signal by wireless communication.

2. The medical system according to claim 1, wherein the CPU is further configured to control a transmission amount of the first sensor signal based on the communication state.

3. The medical system according to claim 1, further comprising a plurality of insertion aids that includes:
the first insertion aid; and
a plurality of communication circuits that includes the first communication circuit, wherein
the second communication circuit is further configured to perform the wireless communication with the plurality of communication circuits, and
the plurality of insertion aids is insertable into the living body.

4. The medical system according to claim 3, wherein the CPU is further configured to select the first communication circuit from the plurality of communication circuits.

5. The medical system according to claim 4, wherein the CPU is further configured to select the first communication circuit based on at least one of
a communication state between the second communication circuit and each communication circuit of the plurality of communication circuits, or
a distance between the second communication circuit and each communication circuit of the plurality of communication circuits.

6. The medical system according to claim 4, wherein the second communication circuit is further configured to transmit the first sensor signal to each communication circuit of the plurality of communication circuits.

7. The medical system according to claim 1, wherein
the insertion part further includes an antenna, and
the second communication circuit is further configured to perform the wireless communication with the first communication circuit in the living body via the antenna.

8. The medical system according to claim 7, further comprising a surgical tool insertable into the living body, wherein
the surgical tool includes a third communication circuit, and
the second communication circuit is further configured to communicate with the third communication circuit via the first communication circuit.

9. The medical system according to claim 1, wherein the sensor includes an image sensor.

10. The medical system according to claim 9, further comprising an information processing device, wherein
the endoscope further includes a connection part connectable to a communication cable, and
the second communication circuit is further configured to transmit, to the information processing device, the first sensor signal via the communication cable.

11. The medical system according to claim 1, wherein the second communication circuit is further configured to perform the wireless communication with the first communication circuit based on a frequency of a millimeter-wave frequency band.

12. The medical system according to claim 1, wherein the first communication circuit is configured to relay a first communication network inside the living body and a second communication network outside the living body.

13. The medical system according to claim 12, wherein
the first insertion aid further includes a first antenna at a first part of the first insertion aid,
the first part of the first insertion aid is insertable into the living body, and
the first communication circuit is further configured to perform the wireless communication with the second communication circuit via the first antenna.

14. The medical system according to claim 13, wherein
the first insertion aid further includes a second antenna at a second part of the first insertion aid,
the second part of the first insertion aid is not insertable into the living body, and
the first communication circuit is further configured to perform communication in the second communication network via the second antenna.

15. The medical system according to claim 1, further comprising:
an information processing device; and
a relay configured to transmit the first sensor signal to the information processing device,
wherein the first communication circuit is configured to perform wired communication with the relay via a communication cable.

16. The medical system according to claim 15, wherein the relay is on a bed on which the living body is placeable.

17. The medical system according to claim 1, further comprising:
a relay in contact with the living body; and
a second insertion aid that includes a third communication circuit, wherein
the first communication circuit is configured to perform human body communication with one of the relay or the third communication circuit by application of a current to the living body.

18. The medical system according to claim 1, further comprising a surgical tool,
wherein the first communication circuit is configured to:
receive the first sensor signal from the second communication circuit;
receive a second sensor signal from the surgical tool; and
add a time stamp to the received first sensor signal and the received second sensor signal.

19. The medical system according to claim 10, wherein the first communication circuit is detachable from the first insertion aid.

20. A communication method, comprising:
in a medical system:
obtaining, by a sensor, data related to a living body;
outputting, by the sensor, a sensor signal that includes the data, wherein
the sensor is one of inside an insertion part of an endoscope or connectable to the insertion part,
the insertion part is insertable into the living body via an insertion aid,
the insertion aid includes a first communication circuit, and
the endoscope includes a second communication circuit and a central processing unit (CPU);
selecting, by the CPU, a communication path of the sensor signal from a first communication path that passes through the first communication circuit and a second communication path that does not pass through the first communication circuit,
wherein the selection of the communication path is based on at least one of
a communication state between the first communication circuit and the second communication circuit, or
a distance between the first communication circuit and the second communication circuit; and
transmitting, by the second communication circuit, based on the selected communication path, the sensor signal by wireless communication.

21. An imaging device, comprising:
an insertion part insertable into a living body via an insertion aid,
wherein the insertion aid includes a first communication circuit;
an image sensor that is one of inside the insertion part or connectable to the insertion part,
wherein the imaging sensor is configured to:
image an inside of the living body; and
output an image signal that includes the image;
a second communication circuit; and
a central processing unit (CPU) configured to select a communication path of the image signal from a first communication path that passes through the first communication circuit and a second communication path that does not pass through the first communication circuit, wherein
the selection of the communication path is based on at least one of
a communication state between the first communication circuit and the second communication circuit, or
a distance between the first communication circuit and the second communication circuit, and
the second communication circuit is configured to transmit, based on the selected communication path, the image signal by wireless communication.

22. An information processing device, comprising:
a first communication circuit configured to receive a sensor signal from a sensor, wherein
the sensor is one of inside an insertion part of an endoscope or connectable to the insertion part,
the insertion part is insertable into a living body via an insertion aid,
the insertion aid includes a second communication circuit,
the endoscope includes a third communication circuit, and
the sensor obtains data related to the living body and outputs the sensor signal that includes the data; and
a central processing unit (CPU) configured to:
select a communication path of the sensor signal from a first communication path that passes through the second communication circuit and a second communication path that does not pass through the second communication circuit, wherein
the selection of the communication path is based on at least one of
a communication state between the second communication circuit and the third communication circuit, or
a distance between the second communication circuit and the third communication circuit;
control the first communication circuit to receive the sensor signal based on the selected communication path; and
control a transmission amount of the sensor signal based on the at least one of the communication state or the distance.

23. An endoscope system, comprising:
an insertion aid that includes a first communication circuit; and
an endoscope that includes:
an insertion part insertable into a living body via the insertion aid;
an image sensor that is one of inside the insertion part or connectable to the insertion part,
wherein the image sensor is configured to:
image an inside of the living body; and
output an image signal that includes the image;
a second communication circuit; and
a central processing unit (CPU) configured to select a communication path of the image signal from a first communication path that passes through the first communication circuit and a second communication path that does not pass through the first communication circuit, wherein
the selection of the communication path is based on at least one of
  a communication state between the first communication circuit and the second communication circuit, or
  a distance between the first communication circuit and the second communication circuit, and
the second communication circuit is configured to transmit based on the selected communication path, the image signal by wireless communication.

\* \* \* \* \*